United States Patent [19]

Hasegawa et al.

[11] Patent Number: 5,268,290
[45] Date of Patent: Dec. 7, 1993

[54] PROCESS FOR PRODUCING NEURAMINIDASE

[75] Inventors: Mamoru Hasegawa, Kawasaki; Kazuhiro Sakurada, Machida, both of Japan

[73] Assignee: Kyowa Hakko Kogyo Co., Ltd., Tokyo, Japan

[21] Appl. No.: 384,709

[22] Filed: Jul. 25, 1989

[30] Foreign Application Priority Data

Jul. 26, 1988 [JP] Japan .................. 63-186441
Mar. 31, 1989 [JP] Japan .................. 1-81199

[51] Int. Cl.$^5$ .................. C12N 9/26; C12N 15/56; C12N 15/76
[52] U.S. Cl. .................. 435/201; 435/69.1; 435/200; 435/252.35; 435/320.1; 536/23.2
[58] Field of Search .................. 435/69.1, 172.3, 320.1, 435/252.3, 252.35; 536/27, 23.2

[56] References Cited

U.S. PATENT DOCUMENTS

4,710,470 12/1987 Uwajiwa et al. .................. 435/200
5,024,948 6/1991 Rothstein et al. .................. 435/252.1

FOREIGN PATENT DOCUMENTS

0133694 3/1985 European Pat. Off.
50-11991 5/1975 Japan.
60-34181 2/1985 Japan.

OTHER PUBLICATIONS

Chemical Abstracts, vol. 108, part 23, Jun. 6, 1988, p. 181, abstract No. 199433v, Vimret al.: "Cloning and expression of the *Vibrio cholerae* neuraminidase gene nanH in *Escherichia coli*".
Journal of Bacteriology, vol. 170, No. 1, Jan. 1988, pp. 71-77 American Society for Microbiology, Baum t al.: "Temporally *micromonospora echinospora*".
Sialidase a. The Origin and distribution of salidase. Sialidase is widely distributed in a variety of tissues of mammals, and fowls as well as microorganism of virus, bacillus and actinomyces. It's origin and distribution is shown in table 1. b. Purification of enzyme and the measuring method of enzyme activity c. various enzymological characteristics d. Biological significance.
Lotvin, J. et al., 1986, Abstracts of the 86th Annual Meeting of the American Society for Microbiology, p. 148, No. H-125.
Lin, J. and Y. Xue, 1986 (Abstract) in Szabo, G., et al., Eds., Symposium Biologica Hungarica 32: 422.
Uchida, Y., et al, 1974, Biochimica et Biophysica Acta 350: 425–431.
Katz, E., et al., 1983, Journal of General Microbiology 129: 2703-2714.
Chater, K., et al., 1983, Current Topics in Microbiology and Immunobiology 96: 69-95.
Sanger, F., et al., 1977, Proc. Nat'l. Acad. Sci. USA 74(12): 5463-5467.
Tabor, S. and C. Richardson (1987) Proc. Nat'l. Acad. Sci. USA 84: 4767-4771.
Vieira, J. and J. Messing, 1987, Methods in Enzymology 153: 3-11.
Aisaka, K., et al., 1987, FEMS Microbiology Letters 44: 289-291.
Peberdy, J. F., et al., 1985, in Greenwood, D., et al., Eds., Symposium of the Society for General Microbiology, 38, Cambridge University Press, New York, N.Y. pp. 283-322.

*Primary Examiner*—Robert A. Wax
*Assistant Examiner*—William W. Moore
*Attorney, Agent, or Firm*—Cushman, Darby & Cushman

[57] ABSTRACT

Streptomyces lividans transformed with a recombinant DNA containing a DNA fragment which is derived from Micromonospora viridifaciens and which comprises a DNA sequence encoding a neuraminidase as well as flanking sequence regions is cultured, and neuraminidase can be efficiently recovered from the culture. Neuraminidase is utilized for clinical diagnosis of inflammatory diseases, diffuse collagen diseases, cancer, etc.

10 Claims, 2 Drawing Sheets

PROCESS FOR PRODUCING NEURAMINIDASE

BACKGROUND OF THE INVENTION

The present invention relates to a process for producing neuraminidase. Neuraminidase (EC 3.2.1.18) is a hydrolase, of which substrate is a ketoside having an α-configuration in sialic acid residues (acyl derivatives of neuraminic acid are collectively called sialic acid) located at the ends of glycoproteins, glycolipids, etc., important constituents of the living body, and which is capable of releasing the sialic acid residues.

Neuraminidase is used for quantitative determination of sialic acid-containing substances in the living body, such as sera, etc., and utilized in the field of clinical diagnosis of various inflammatory diseases, diffuse collagen diseases, cancer, etc.

It is known that neuraminidase is widely distributed in microorganisms such as viruses, bacteria, actinomycetes, etc., various tissues from fowls, mammals, etc.

For the production of neuraminidase by using microorganisms, there have been known various processes wherein a microorganism capable of producing neuraminidase is cultured in a medium supplemented with a neuraminidase inducer such as colominic acid, a leach and extract of various animal tissues, and neuraminidase formed is recovered therefrom [Metabolism, 16 (5), 761 (1979); Biochim. Biophys. Acta, 350, 425–431 (1974); J. Biochem., 82, 1425–1433 (1977); J. Bacteriol., 119 (2), 394–400 (1974); Canadian J. Microbiology, 18, 1007 (1972); Japanese Published Examined Patent Application No. 11991/1975; and Japanese Published Unexamined Patent Application No. 34181/1985 (U.S. Pat. No. 4710470, EP 133694-A)].

It is extremely disadvantageous from an economical viewpoint to use neuraminidase inducers in large quantities upon production of neuraminidase. In order to produce neuraminidase at low costs in an industrial scale, it is necessary to use a microorganism which has excellent neuraminidase productivity and requires no neuraminidase inducer.

SUMMARY OF THE INVENTION

The present inventors have made various investigations on processes for producing neuraminidase at low costs in an industrial scale. As a result, it has been found that by cloning a DNA fragment harboring a gene encoding neuraminidase and introducing a recombinant DNA containing the DNA fragment into a host microorganism, neuraminidase productivity of the host microorganism can be increased and neuraminidase can be produced without supplementing any neuraminidase inducer, and the present invention has been accomplished.

The present invention provides a process for producing neuraminidase which comprises culturing in a medium a microorganism belonging to the genus Streptomyces and harboring a recombinant DNA containing a DNA fragment which is derived from a microorganism belonging to the genus Micromonospora and carries thereon genetic information that participates in the synthesis of neuraminidase, accumulating neuraminidase in the culture; and recovering neuraminidase from the culture.

Figure 1:
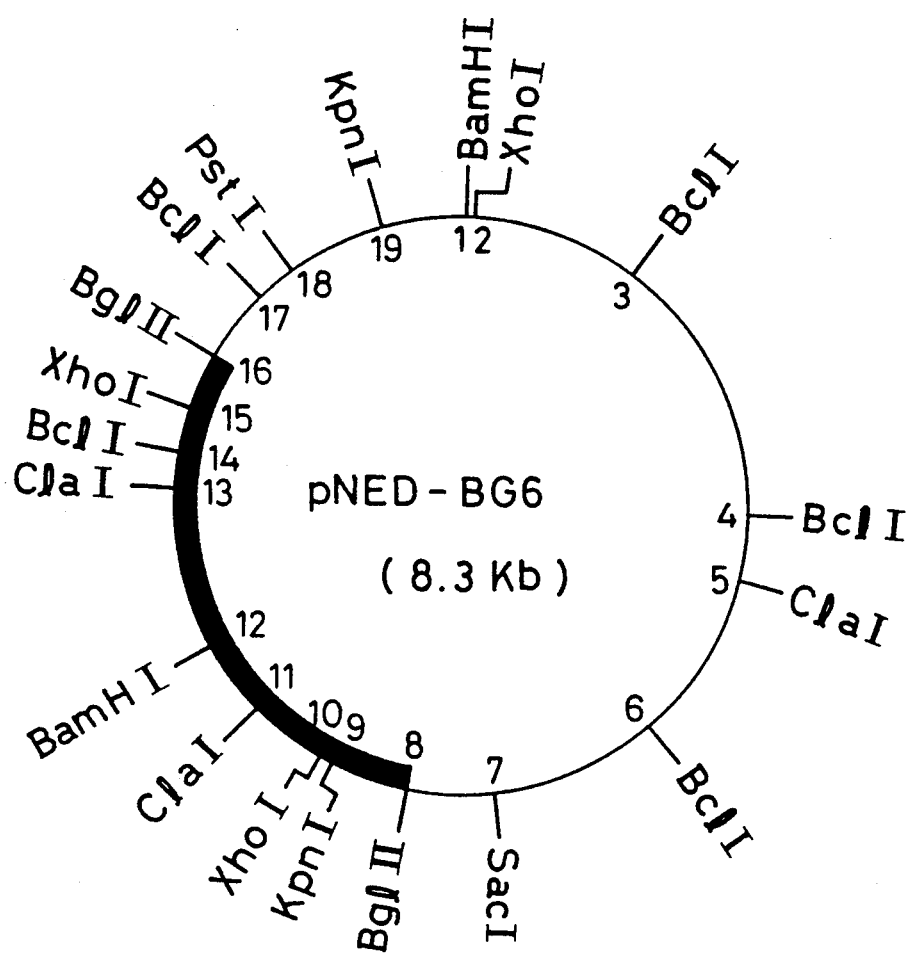
FIGS. 1 and 2 illustrate the cleavage maps for restriction enzymes of plasmids pNED-BG6 and NED-BC4, respectively. In the figures, bold portion shows a region containing a gene encoding neuraminidase, and numerals indicate the following values (kb).

| FIG. 1 | | |
|---|---|---|
| 1: 0.00/8.30 | 2: 0.04 | 3: 0.85 |
| 4: 2.10 | 5: 2.40 | 6: 3.21 |
| 7: 4.15 | 8: 4.40 | 9: 4.80 |
| 10: 4.85 | 11: 5.20 | 12: 5.55 |
| 13: 6.30 | 14: 6.44 | 15: 6.65 |
| 16: 6.90 | 17: 7.25 | 18: 7.42 |
| 19: 7.90 | | |

Figure 2:
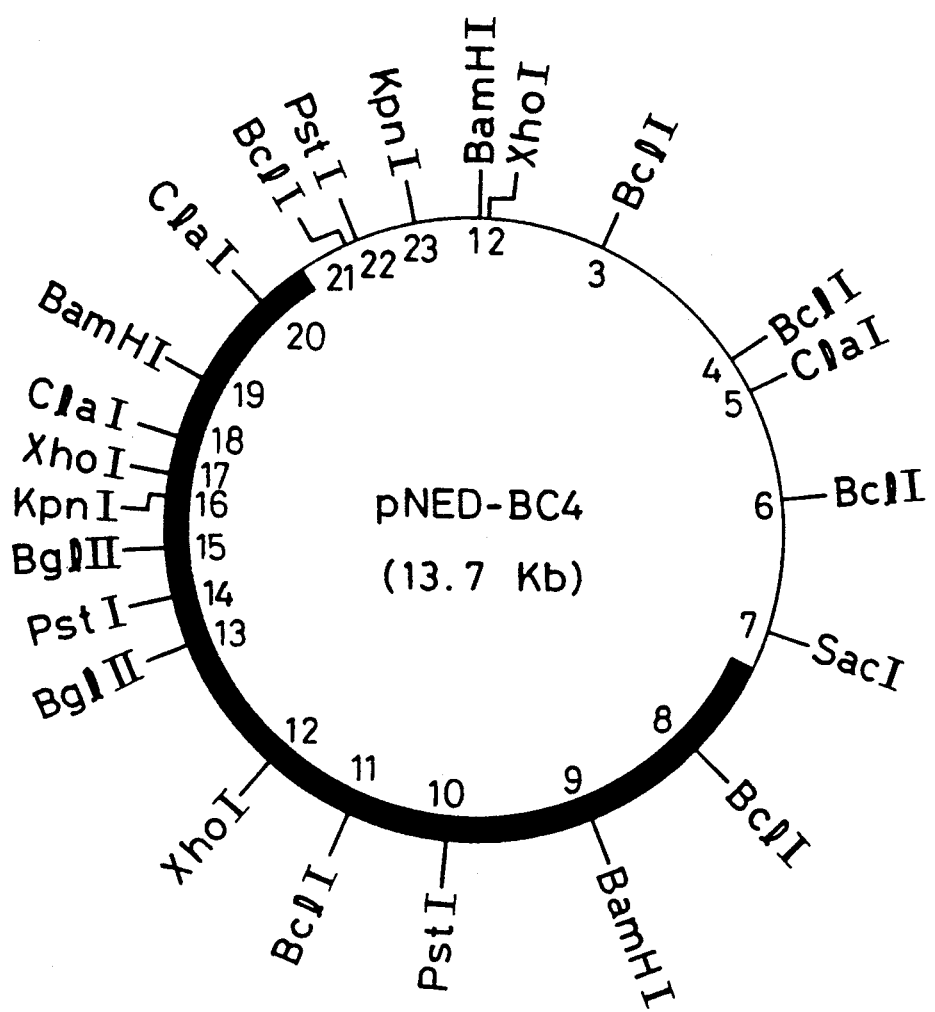

| FIG 2 | | |
|---|---|---|
| 1: 0.00/13.7 | 2: 0.04 | 3: 0.85 |
| 4: 2.10 | 5: 2.40 | 6: 3.21 |
| 7: 4.15 | 8: 5.10 | 9: 6.00 |
| 10: 7.08 | 11: 7.82 | 12: 8.45 |
| 13: 9.43 | 14: 9.77 | 15: 10.00 |
| 16: 10.50 | 17: 10.65 | 18: 10.88 |
| 19: 11.35 | 20: 12.05 | 21: 12.70 |
| 22: 12.77 | 23: 13.25 | |

DETAILED DESCRIPTION OF THE INVENTION

Hereafter the present invention is described in more detail.

As a source for providing a DNA fragment carrying thereon genetic information that participates in the synthesis of neuraminidase, mention may be made of chromosomal DNA of a microorganism belonging to the genus Micromonospora and capable of producing neuraminidase. Specific examples of strains are as follows.

*Micromonospora chalcea* ATCC 12452
*Micromonospora chalcea* ATCC 27084
*Micromonospora citrea* NRRL B-16601
*Micromonospora echinospora* ATCC 15837
*Micromonospora purpureochromogenes* NRRL B-943
*Micromonospora globosa* NRRL B-2673
*Micromonospora melanospora* IFO 12515
*Micromonospora narashino* ATCC 27331
*Micromonospora viridifaciens* ATCC 31146

The chromosomal DNA of the strains described above can be extracted in the manner later shown in Example 1 and used as a source for providing a DNA fragment carrying thereon genetic information that participates in the synthesis of neuraminidase.

As a vector for inserting a DNA fragment carrying thereon genetic information that participates in the synthesis of neuraminidase, any vector is usable so long as it is able to autonomously replicate in strains belonging to the genus Streptomyces. Preferred examples include pIJ41 [Gene, 20, 51–62 (1982)], pIJ702 [J. Gen. Microbiol., 129, 2703–2714 (1983)], etc.

Recombinant DNAs containing a DNA fragment comprising a DNA sequence encoding a neuraminidase as well as flanking sequence regions can be obtained with a mixture of various recombinant DNAs by cleaving a donor DNA and a vector DNA with appropriate restriction enzymes, for example, Bgl II or Bcl I, and ligating them by utilizing their cleavage terminals. Microorganisms incapable of producing neuraminidase are transformed by using the thus obtained recombinant DNAs. By examining neuraminidase productivity of the thus obtained transformants, a transformant which has acquired neuraminidase productivity is selected. Recombinant DNAs containing a DNA fragment comprising a DNA sequence encoding a neuraminidase as well as flanking sequence regions can be obtained by extracting from the thus obtained transformant.

As host microorganisms, any microorganisms are usable so long as they belong to the genus Streptomyces and can acquire neuraminidase productivity by maintaining a recombinant DNA according to the present invention. Specifically, the following strains can be used.

*Streptomyces lividans* TK23
*Streptomyces lividans* ATCC 19844
*Streptomyces ambofaciens* ATCC 15154
*Streptomyces ambofaciens* ATCC 23877
*Streptomyces ambofaciens* IFO 12651
*Streptomyces fradiae* ATCC 10745
*Streptomyces fradiae* NRRL B-2702
*Streptomyces glaucescens* ATCC 23622

A strain capable of producing neuraminidase can be obtained by transforming one of the host microorganisms described above with a recombinant DNA containing a DNA fragment comprising a DNA sequence encoding a neuraminidase as well as flanking sequence regions in accordance with the method of K. F. Chater et al. [Current Topics in Microbiology and Immunology, 96, 69-95 (1982)].

Specific examples of the microorganisms which can be used in the present invention include *Streptomyces lividans* NED-BG6 maintaining recombinant DNA pNED-BG6 obtained by inserting into pIJ702, a *Micromonospora viridifaciens*-derived DNA fragment comprising a DNA sequence encoding a neuraminidase as well as flanking sequence regions and *Streptomyces lividans* NED-BC4 maintaining the recombinant DNA pNED-BC4 obtained in a similar manner. These strains have been deposited with the Fermentation Research Institute, Agency of Industrial Science and Technology of Japan under the Budapest Treaty on Feb. 27, 1988 and Mar. 17, 1989 under accession Nos. FERM BP-1768 and FERM BP-2340, respectively.

The transformants having neuraminidase productivity which are obtained in the present invention are cultured in a manner conventionally employed for the cultivation of ordinary actinomycetes without supplementing any neuraminidase inducer and they produce and accumulate neuraminidase in the culture.

In the present invention, any natural medium and synthetic medium may be used so long as carbon sources, nitrogen sources, inorganic substances and other nutrients are suitably contained therein.

As carbon sources, there can be used various carbohydrates, such as glucose, fructose, sucrose, maltose, mannose, starch, starch hydrolysate, molasses, etc.; various sugar alcohols, such as glycerol, sorbitol, mannitol, etc.; various organic acids, such as acetic acid, lactic acid, pyruvic acid, fumaric acid, citric acid, etc.; various alcohols, such as ethanol, etc.; various glycols, such as ethylene glycol, propylene glycol, etc.; various amino acids, a leaching solution of bovine heart of bovine brain, bovine blood powders, etc.

As nitrogen sources, there can be used ammonia or various inorganic and organic ammonium salts, such as ammonium chloride, ammonium carbonate, ammonium phosphate, ammonium nitrate, ammonium acetate, etc.; nitrates such as sodium nitrate, potassium nitrate, etc.; urea, amino acids and other nitrogen compounds, as well as nitrogen-containing organic compounds, such as peptone, NZ-amine, meat extract, corn steep liquor, casein hydrolysate, chrysalis hydrolysate, fish meal or its digestion products, defatted soybean or digestion products thereof, etc.

As inorganic substances, there can be used potassium dihydrogenphosphate, dipotassium hydrogenphosphate, potassium chloride, magnesium sulfate, manganese sulfate, ferrous sulfate, sodium chloride, calcium carbonate, etc.

The cultivation is carried out at a pH of 6.0 to 7.5 and a temperature of 25° to 35° C. for 4 to 6 days under aerobic conditions while agitating.

By culturing so, neuraminidase is produced and accumulated in the culture. Neuraminidase can be recovered from the culture as follows.

After completion of the cultivation, the culture is filtered or centrifuged and the cells are removed to obtain the filtrate or supernatant. The filtrate or supernatant is treated in a conventional manner generally used for the purification of enzymes. For example, methods such as salting out, precipitation with organic solvents, dialysis, ion exchange column chromatography, gel filtration chromatography, freeze drying, etc. can be employed to recover purified neuraminidase.

For example, the filtrate of a culture may be subjected to salting out with 50% saturation with ammonium sulfate. The precipitates formed are dissolved in a buffer and then the solution is dialyzed. The dialysate then is adsorbed on a column packed with an anionic exchange resin, such as DEAE-Sephadex or DEAE-cellulose. The adsorbed enzyme is eluted with density gradient of sodium chloride or ammonium sulfate. The eluted enzyme is further purified by gel filtration with Sephadex G-75 or Biogel P-100.

Hereafter the present invention is illustrated by the preferred embodiments.

Example 1

(Step 1) Chromosomal DNA of *Micromonospora viridifaciens* ATCC 31146 was extracted as described below. *Micromonospora viridifaciens* ATCC 31146 was inoculated into 4 ml of SK No. 2c medium [20 g of stabirose K (manufactured by Matsutani Chemical Industry Co., Ltd.), 5 g of glucose, 5 g of yeast extract (manufactured by Daigo Nutrient Chemical Co., Ltd.), 5 g of peptone (manufactured by Kyokuto Pharmaceutical Industry Co., Ltd.), 3 g of yeast extract (manufactured by Kyokuto Pharmaceutical Industry Co., Ltd.), 0.2 g of $KH_2PO_4$, 0.6 g of $MgSO_4.7H_2O$ and 1 g of $CaCO_3$ were made up to 1 liter by adding deionized water thereto, pH of which was adjusted to 7.6; autoclaved at 120° C. for 20 minutes] followed by shaking the culture at 30° C. for 3 days. The entire amount was inoculated into 30 ml of SK No. 2 medium (SK No. 2c medium described above, from which $CaCO_3$ was omitted) followed by further shaking the culture at 30° C. for 2 days. The culture was then centrifuged at 12,000 rpm, 4° C. for 10 minutes to collect the cells. The cells were washed twice with 20 ml of 10.3% sucrose solution. The cells were suspended in 6 ml of TS buffer [50 mM Tris[tris(hydroxymethyl)aminomethane]-hydrochloride buffer (pH 8.0) containing 10.3% sucrose and 25 mM disodium ethylenediaminetetraacetate (EDTA)] and 50 mg of albumen lysozyme was further added to the suspension followed by incubation at 37° C. for an hour. Then 0.6 ml of proteinase K (manufactured by Sigma Inc; its concentration was adjusted to 2 mg/ml with TS buffer) and 3.6 ml of 3.3% sodium dodecyl sulfate solution, were added thereto and the resulting mixture was incubated at 37° C. for an hour to cause lysis. After heating at 50° C. for 30 minutes, the system was placed in a water bath to cool.

Ten ml of a phenol-chloroform mixture [the lower layer obtained by thoroughly admixing 500 g of phenol, 500 ml of chloroform and 800 mg of 8-hydroxyquinoline (manufactured by Tokyo Chemical Industry Co., Ltd.) followed by the addition of 200 ml of deionized water and a thorough shaking of the mixture] was added thereto, and the mixture was gently agitated and then centrifuged at 12,000 rpm, 4° C. for 15 minutes. The upper layer was taken out, and ribonuclease was added thereto up to a final concentration of 20 μg/ml followed by incubation at 37° C. for 45 minutes. 1/10 volume of 5M sodium chloride solution and ¼ volume of polyethylene glycol 6,000 (manufactured by Nakarai Chemical Co., Ltd.) were added thereto, and the mixture was stirred gently. Under ice cooling, the mixture was allowed to stand overnight and then centrifuged at 5,000 rpm, 4° C. for 5 minutes to give pellets, which were then dissolved in 5 to 10 ml of TE buffer. After 1/10 volume of 3M sodium acetate and 1/30 volume of 66 mM $MgCl_2$ solution had been added, 2.2 volume of 99% cold ethanol was added to the mixture. The mixture was slowly agitated and then centrifuged at 5,000 rpm at 4° C. for 5 minutes to give pellets. These pellets were washed twice with 70% cold ethanol to extract chromosomal DNA of *Micromonospora viridifaciens*. The thus obtained chromosomal DNA, 5 μg, was added to 100 μl of M buffer [with respect to its composition, see Manual for Genetic Engineering (Cold Spring Harbour Laboratories), page 228 (1980)] containing 15 units of restriction enzyme Bgl II (manufactured by Boehringer GmbH) followed by reacting at 37° C. for 3 hours. To the reaction mixture was added 100 μl of phenol-chloroform mixture, and the mixture was vigorously agitated for 10 seconds to terminate the reaction. Thereafter, the mixture was centrifuged at 12,000 rpm, 4° C. for 5 minutes to obtain the supernatant.

5 μg vector pIJ702 for actinomyces was added to 40 μl of M buffer containing 5 units of restriction enzyme Bgl II, and the mixture was incubated at 37° C. for 2 hours. Then, 50 μl of deionized water and 10 μl of 1M Tris-hydrochloride buffer (pH 8.5) were added to the reaction mixture. The system was thoroughly mixed. Furthermore, 2.5 units of bovine small intestine alkaline phosphatase (for molecular biology, manufactured by Boehringer GmbH) was added thereto, followed by incubation at 37° C. for 45 minutes. Then, 100 μl of phenol-chloroform mixture was added thereto. After vigorous stirring for 10 seconds, the mixture was centrifuged at 12,000 rpm, 4° C. for 5 minutes to obtain a supernatant.

25 μl of the thus obtained supernatant, containing 5 μg of chromosomal DNA of *Micromonospora viridifaciens* ATCC 31146 was mixed with 25 μl of the thus obtained supernatant containing 5 μg of pIJ702. The mixture was thoroughly mixed with 1/10 volume of 3M sodium acetate solution and an equal volume of isopropanol. Under ice cooling, the mixture was allowed to stand for 30 minutes. Then, the mixture was centrifuged at 14,000 rpm, 4° C. for 5 minutes to yield pellets. These pellets were washed with 400 μl of 70% cold ethanol and dried in vacuo. To the pellets was added 25 μl of ligation buffer (pH 7.6) composed of 66 mM Tris-hydrochloride buffer containing 0.8 mM ATP (adenosine triphosphate, manufactured by Sigma Inc.), 10 mM dithiothreitol (manufactured by Nakarai Chemical Co., Ltd.) and 6.6 mM magnesium chloride to dissolve the pellets. Furthermore, 1 unit of T4 ligase (manufactured by Boehringer GmbH) was added to the solution, followed by incubation at 15° C. for 15 hours.

To the reaction solution were sequentially added 75 μl of P-medium [10.3 g of sucrose, 25 mg of $K_2SO_4$, 203 mg of $MgCl_2.6H_2O$ and 0.2 ml of trace metal solution [solution containing 40 mg of $ZnCl_2$, 200 mg of $FeCl_3.6H_2O$, 10 mg of $CuCl_2.2H_2O$, 10 mg of $MnCl_2.4H_2O$, 10 mg of $Na_2B_4O_7.10H_2O$ and 10 mg of $(NH_4)_6Mo_7O_{24}.4H_2O$ in 1 liter of deionized water] was mixed with deionized water to make 90 ml. Thereto were added 10 ml of 0.25M TES [N-tris(hydroxymethyl)-methyl-2-aminoethanesulfonic acid, manufactured by Nakarai Chemical Co., Ltd.] buffer (pH 7.2), 0.5 ml of 5M calcium chloride solution and 1 ml of 0.5% $KH_2PO_4$; all solutions used were sterilized in an autoclave and 25 μl of bacterial protoplast suspension of *Streptomyces lividans* TK23 prepared according to the method of K. F. Chater et al. [Current Topics in Microbiology and Immunology, 96, 69-95 (1982)] and gently mixed. The mixture was allowed to stand at room temperature for a minute. Then, 500 μl of T-medium [a mixture of 25 vol % polyethylene glycol 1000 (manufactured by Nakarai Chemical Co., Ltd.) and 75 vol % P-medium] was added to the mixture and stirred. The mixture was appropriately diluted with P-medium, and 100 μl portions of the suspension was coated onto a regeneration plate R5 [103 g of sucrose, 0.25 g of $K_2SO_4$, 10.12 g of $MgCl_2.6H_2O$, 10 g of glucose, 1 g of Casamino acid (manufactured by Difco Inc.), 5 g of yeast extract (manufactured by Difco Inc.), 2 ml of trace metal solution, 5.73 g of TES and 2.5 g of NaOH were made 1 liter with deionized water, and its pH was adjusted to 7.2. The mixture was divided into 5 aliquot portions and 4.4 g of Bactoagar (manufactured by Difco Inc.) was added to each aliquot, followed by sterilization for 20 minutes under high pressure. To each of them were added 3 ml of 20% sodium glutamate solution, 3 ml of 2% $NaNO_3$ solution, 2 ml of 0.5% $KH_2PO_4$ solution and 0.8 ml of 5M $CaCl_2$. The mixture was thoroughly mixed and 20 ml portions of the mixture were inoculated on plates and dried for 1.5 hours. The dried ones were used]. After culturing at 30° C. for 15 hours, 2.5 ml of soft agar medium [8 g of nutrient broth (manufactured by Difco Inc.) and 5 g of bactoagar were sterilized together with 1 liter of deionized water in an autoclave] containing thiopeptin (manufactured by Fujisawa Pharmaceutical Co., Ltd.) in a concentration of 0.5 mg/ml was overlaid, followed by culturing at 30° C. for 3 days. On plates on which regenerated transformants grew, 2.5 ml of soft agar medium containing 2 mg of 4-methylumbelliferyl-N-acetylneuraminic acid ammonium salt (manufactured by Nakarai Chemical Co., Ltd.) was overlaid thereon, followed by incubation at 37° C. for 5 minutes. The medium was irradiated with a UV lamp, so as to detect transformants which emit fluorescence. Thus, 121 neuraminidase-producing transformants were obtained. With respect to each transformant obtained, neuraminidase production test was conducted under conditions similar to those in Example 2 described herein below. A few strains having excellent neuraminidase productivity were selected, and a plasmid possessed by one of the strains was isolated. Analysis of its structure by digestion with various restriction enzymes and agarose gel electrophoresis revealed that the plasmid had the structure as shown in FIG. 1. This plasmid was named pNED-BG6.

(Step 2) A recombinant DNA containing a DNA fragment comprising a DNA sequence encoding a neuraminidase as well as flanking sequence regions was constructed from the chromosomal DNA of *Micromonospora viridifaciens* prepared in (Step 1) described above in a manner similar to (Step 1) except that restriction enzyme Bcl I was used instead of Bgl II.

That is, 5 μg of the chromosomal DNA was added to 100 μl of M-buffer containing 15 units of the restriction enzyme Bcl I (manufactured by Boehringer Mannheim GmbH), and the mixture was reacted at 50° C. for 2 hours. After 100 μl of phenol-chloroform mixture had been added thereto with vigorous agitation, the resulting mixture was centrifuged at 12,000 rpm, 4° C. for 5 minutes to give the supernatant. Vector pIJ702 for actinomycetes was cleaved with the restriction enzyme Bgl II and treated with bovine small intestine alkaline phosphatase and then with a phenol-chloroform mixture in a manner similar to (Step 1) described above; and the product was added to the supernatant. To the mixture was added 1/10 volume of 3M sodium acetate solution and an equal volume of isopropanol, based on the volume of the mixture. After thoroughly mixing, the mixture was allowed to stand for 30 minutes under ice cooling. The mixture was then centrifuged at 14,000 rpm, 4° C. for 5 minutes to give pellets. The pellets were washed with 400 μl of 70% cold ethanol and dried in vacuo. To the pellets was added 25 μl of ligation buffer to dissolve the pellets. One unit of T4 ligase was then added to the solution, followed by incubation at 15° C. for 15 hours.

To the reaction solution was added 75 μl of P-medium and 25 μl of the bacterial protoplast suspension of *Streptomyces lividans* TK23 prepared in (Step 1) described above, and the mixture was gently mixed. The protoplast was transformed in a similar manner as in (Step 1) above. After appropriately diluted with P-medium, the suspension was spread onto regeneration plate R5. After culturing at 30° C. for 15 hours, 2.5 ml of soft agar medium containing thiopeptin was overlaid thereon, followed by culturing at 30° C. for 3 days. As in (Step 1) described above, transformants emitting fluorescence around colonies were detected using 4-methylumbelliferyl-N-acetylneuraminic acid. Twenty-seven neuraminidase-producing strains were thus produced. With respect to each transformant obtained, a neuraminidase production test was performed under conditions similar to Example 2 described hereinbelow. A strain having excellent neuraminidase productivity was selected, and a plasmid possessed by the strain was isolated. Analysis of its structure by digestion with various restriction enzymes and agarose gel electrophoresis revealed that the plasmid had the structure as shown in FIG. 2. This plasmid was named pNED-BC4.

Example 2

Production of neuraminidase by microorganisms maintaining recombinant DNA:

*Streptomyces lividans* NED-BG6 (FERM BP-1768) maintaining pNED-BG6 obtained in Example 1 and *Streptomyces lividans* NED-BC4 (FERM BP-2340) maintaining pNED-BC4 obtained in Example 1 were inoculated in 4 ml each of YEME medium [a medium containing 3.0 g of yeast extract (manufactured by Difco Inc.), 5.0 g of bactopeptone (manufactured by Difco Inc.) and 10.0 g of glucose in 1 liter of deionized water, adjusted to a pH of 7.2 and autoclaved at 120° C. for 20 minutes] containing 1 μg of thiopeptin, followed by shaking culture at 30° C. for 2 days. 0.5 ml of the thus obtained seed culture, was inoculated in 10 ml of SK No. 2 medium containing 2.5 μg of thiopeptin, followed by shaking the culture at 30° C. for 5 days. During the culturing, 0.2 ml each of the culture broth was subjected to sampling every day.

Each of the cultivation samples were centrifuged at 14,000 rpm at 4° C. for 5 minutes to collect the supernatant. The supernatant was diluted 40-fold with deionized water to 40-fold, and its neuraminidase activity was determined.

Determination of the neuraminidase activity was made in accordance with the quantitative assay for N-acetylhexosamine described in "Protein, Nucleic Acid, Enzyme", separate volume "Experimental Method of Glycosides", page 22 (1968) published by Kyoritsu Publishing Co., Ltd.

To 10 μl of the thus obtained supernatant dilution was added 0.1 ml of sodium colominate (40 mg/ml), 0.1 ml of 0.2M citrate-disodium phosphate buffer (pH 5.0) and 0.3 ml of deionized water, followed by incubation at 37° C. for 10 minutes. The reaction was stopped by heating at 100° C. for 30 minutes. Then, 50 μl of N-acetylneuraminic acid aldolase (1 unit/ml, manufactured by Kyowa Hakko Kogyo Co., Ltd.) was added, followed by incubation at 70° C. for 15 minutes. The N-acethylmannosamine formed was quantitatively assayed by the Morgan-Elson method as described below. That is, 100 μl of borate solution (prepared by dissolving 4.95 g of boric acid in 50 ml of deionized water and adjusting its pH to 9.1, followed by the addition of deionized water to make 100 ml) was added to the above reaction solution. Immediately after being heated at 100° C. for precisely 3 minutes, the reaction mixture was immediately placed in water to cool. To the reaction mixture was added 3 ml of p-dimethylaminobenzaldehyde reagent [which was prepared by dissolving 10 g of p-dimethylaminobenzaldehyde (manufactured by Nakarai Chemical Co., Ltd.) in 100 ml of glacial acetic acid containing 12.5% 10 N hydrochloric acid], and the mixture was thoroughly agitated. After incubation at 37° C. for 30 minutes, the absorbance of the solution at 585 nm was measured. Using a calibration curve prepared by measuring absorbance of N-acetylmannosamine having known concentrations at 585 nm, the quantity of N-acetylmannosamine formed was calculated, and the neuraminidase activity in the supernatant was determined. In this case, the amount of enzyme necessary to produce 1μ mol of N-acetylmannosamine in a minute was defined as 1 unit. The neuraminidase activity in the supernatant is shown in Table 1.

TABLE 1

| Strain | Neuraminidase Activity (unit/ml) | | | | |
|---|---|---|---|---|---|
| | Day 1 | Day 2 | Day 3 | Day 4 | Day 5 |
| NED-BG6 | 4 | 27 | 58 | 100 | 118 |
| NED-BC4 | 12 | 26 | 69 | 125 | 136 |

As is shown in Table 1, NED-BG6 and NED-BC4 exhibited neuraminidase activities of 118 unit/ml and 136 unit/ml, respectively. On the other hand, *Micromonospora viridifaciens*, the original strain, showed a maximum of 1.2 units/ml.

Next, 500 ml of the culture of NED-BG6 strain obtained in the same manner as above was centrifuged at 8,000 rpm, 4° C. for 10 minutes to obtain a supernatant.

Ammonium sulfate (manufactured by Nakarai Chemical Co., Ltd.) was gradually added to the supernatant to 50% saturation. The mixture was allowed to stand at 4° C. overnight and then centrifuged at 10,000 rpm, 4° C. for 10 minutes to give pellets. After the thus obtained pellets had been dissolved in 30 ml of 10 mM phosphate ($NaH_2PO_4$-$Na_2HPO_4$) buffer (pH 7.0), the solution was dialyzed against 2 liters of 10 mM phosphate buffer overnight. The entire solution was gently adsorbed on a column (having an inner diameter of 4.2 cm and a height of 37.5 cm) packed with 500 ml of DEAE-Sepharose CL-6B (manufactured by Pharmacia Fine Chemicals Inc.), and 1 liter of phosphate buffer was passed through the column to remove the non-adsorbed substances.

Then, 1 liter of 10 mM phosphate buffer containing 50 mM NaCl and then 10 mM phosphate buffer containing 100 mM NaCl were passed through the column to collect eluate having an absorbance of 0.2 or more at the wavelength of 280 nm. The eluate was dialyzed against 5 liters of phosphate buffer overnight, and the dialysate was freeze dried. The thus obtained powder contained 282 mg of protein showing $4.2 \times 10^4$ units of enzyme activity. Yield of enzyme from the active supernatant of the culture was 71.2%.

Example 3

The DNA nucleotide sequence of the neuraminidase gene derived from *Micromonospora viridifaciens* was determined as follows. Since it was expected that the neuraminidase gene was present in the regions common to the insert DNAs in recombinant plasmids PNED-BG6 and PNED-BCt produced in Example 1 (positions 8, 9, 10, 11, 12 and 13 in FIG. 1 and positions 15, 16, 17, 18, 19 and 20 in FIG. 2), the common region and the upstream and downstream regions thereof were analyzed.

First, a DNA fragment of 2.5 kb digested with Bgl II (FIG. 1, 8 to 16 positions), derived from pNED-BG6, and a DNA fragment of 0.5 kb digested with Bgl II (FIG. 2, 13 to 15 positions), derived from pNED-BC4, were cloned, respectively, using E. coli cloning vector pUC118 [Methods in Enzymology, 153, 3-11 (1987)]. Since nucleotide sequence is determined using viral single-stranded DNA and primer extension goes only toward one direction to inserted DNA, each DNA fragment was inserted in two directions, so as to make it possible to determine the nucleotide sequence of the inserted DNA fragment from both ends. For example, in the case of the DNA fragment derived from pNED-BG6, there were prepared two cloned products: one inserted with the DNA fragment in the direction of 8 to 16 positions in FIG. 1 (based on the direction of primer extension) and the other inserted in the direction of 16 to 8 positions. The cloning was performed according to the method described in J. Mol. Biol., 53, 159 (1970). Utilizing the same cleavage ends formed by Bgl II and Bam HI, the Bgl II cleaved DNA fragment was inserted into the Bam HI site of pUC118.

From the thus obtained plasmid, the inserted DNA fragment was then excised by using restriction enzymes Pst I and Xba I (both manufactured by Boehringer GmbH), and various deletion mutants were prepared using Kilo-Deletion Kit (manufactured by Takara Shuzo Co., Ltd.). From the deletion mutants obtained, various DNA fragments were recovered with helper phage M13K07 as single stranded DNA, and their base sequence was determined in accordance with the dideoxy method [Proc. Natl. Acad. Sci. USA., 74, 5463-5467 (1977)]. Since the DNA of actinomycetes consists of guanine and cytosine at high molar ratio, a problem of compressed band tends to occur in gel electrophoresis for determining DNA nucleotide sequences. In order to avoid this problem, deoxyguanosine triphosphate (dGTP) and deoxyinosine triphosphate (dITP) were used in combination in the reaction. The DNA nucleotide sequence and amino acid sequence of the neuraminidase gene derived from *Micromonospora viridifaciens* was determined as described above are shown in Table 2.

TABLE 2

```
        10           20           30           40
ATCGCCGGGGCACCCGTCCCGCCCGGCGGCGAGCCGCTCTACACG
Ile Ala Gly Ala Pro Val Pro Pro Gly Gly Glu Pro Leu Tyr Thr 55           65           75           85
GAGCAGGACCTCGCCGTGAACGGCAGGGAGGGCTTTCCGAACTAC
Glu Gln Asp Leu Ala Val Asn Gly Arg Glu Gly Phe Pro Asn Tyr 100          110          120          130
CGCATCCCAGCGCTGACCGTCACGCCCGACGGGGACCTGCTGGCC
Arg Ile Pro Ala Leu Thr Val Thr Pro Asp Gly Asp Leu Leu Ala 145          155          165          175
TCGTACGACGGCCGCCCGACCGGTATCGACGCGCCCGGCCCCAAC
Ser Tyr Asp Gly Arg Pro Thr Gly Ile Asp Ala Pro Gly Pro Asn 190          200          210          220
TCCATCCTCCAACGCCGCAGCACCGACGGCGGCCGGACGTGGGGC
Ser Ile Leu Gln Arg Arg Ser Thr Asp Gly Gly Arg Thr Trp Gly 235          245          255          265
GAGCAACAGGTCGTCAGCGCCGGCCAGACCACCGCGCCGATCAAG
Glu Gln Gln Val Val Ser Ala Gly Gln Thr Thr Ala Pro Ile Lys 280          290          300          310
GGGTTCTCCGACCCCAGCTACCTTGTCGACCGGGAAACCGGGACC
Gly Phe Ser Asp Pro Ser Tyr Leu Val Asp Arg Glu Thr Gly Thr 325          335          345          355
ATCTTCAACTTCCACGTCTACTCCCAGCGGCAGGGCTTCGCCGGC
Ile Phe Asn Phe His Val Tyr Ser Gln Arg Gln Gly Phe Ala Gly
```

-continued

```
            370         380         390         400
AGCCGGCCCGGCACCGACCCGGCAGACCCCAACGTGCTCCACGCC
Ser Arg Pro Gly Thr Asp Pro Ala Asp Pro Asn Val Leu His Ala 415         425         435         445
AACGTCGCGACCTCGACCGACGGCGGTCTGACCTGGTCGCACCGG
Asn Val Ala Thr Ser Thr Asp Gly Gly Leu Thr Trp Ser His Arg 460         470         480         490
ACCATCACGGCCGACATCACCCCGGATCCGGGCTGGCGCAGCCGC
Thr Ile Thr Ala Asp Ile Thr Pro Asp Pro Gly Trp Arg Ser Arg 505         515         525         535
TTCGCCGCCTCCGGCGAAGGCATCCAGCTCCGCTATGGACCCCAC
Phe Ala Ala Ser Gly Glu Gly Ile Gln Leu Arg Tyr Gly Pro His 550         560         570         580
GCCGGTCGACTCATCCAGCAGTACACGATCATCAACGCTGCCGGC
Ala Gly Arg Leu Ile Gln Gln Tyr Thr Ile Ile Asn Ala Ala Gly 595         605         615         625
GCCTTCCAGGCGGTGAGCGTGTACAGCGACGACCACGGAAGGACC
Ala Phe Gln Ala Val Ser Val Tyr Ser Asp Asp His Gly Arg Thr 640         650         660         670
TGGCGCGCCGGCGAAGCCGTCGGGGTCGGCATGGACGAGAACAAG
Trp Arg Ala Gly Glu Ala Val Gly Val Gly Met Asp Glu Asn Lys 685         695         705         715
ACCGTGGAACTCTCCGATGGCCGGGTCCTGCTCAACAGCCGCGAC
Thr Val Glu Leu Ser Asp Gly Arg Val Leu Leu Asn Ser Arg Asp 730         740         750         760
TCGGCCCGCAGCGGATACCGTAAGGTGGCCGTCTCCACTGACGGC
Ser Ala Arg Ser Gly Tyr Arg Lys Val Ala Val Ser Thr Asp Gly 775         785         795         805
GGCCACAGCTACGGCCCGGTGACCATCGACCGCGACCTCCCCGAC
Gly His Ser Tyr Gly Pro Val Thr Ile Asp Arg Asp Leu Pro Asp 820         830         840         850
CCGACGAACAACGCATCGATCATCCGGGCCTTCCCTGACGCCCCG
Pro Thr Asn Asn Ala Ser Ile Ile Arg Ala Phe Pro Asp Ala Pro 865         875         885         895
GCCGGCTCCGCGCGGGCCAAGGTCCTGCTCTTCTCCAACGCCGCC
Ala Gly Ser Ala Arg Ala Lys Val Leu Leu Phe Ser Asn Ala Ala 910         920         930         940
AGCCAGACCTCGCGCAGTCAGGGCACCATCCGGATGTCCTGCGAC
Ser Gln Thr Ser Arg Ser Gln Gly Thr Ile Arg Met Ser Cys Asp 955         965         975         985
GATGGCCAGACCTGGCCGGTTTCGAAGGTCTTCCAGCCCGGCTCG
Asp Gly Gln Thr Trp Pro Val Ser Lys Val Phe Gln Pro Gly Ser 1000        1010        1020        1030
ATGTCGTACTCCACCCTGACCGCACTGCCCGACGGCACCTACGGG
Met Ser Tyr Ser Thr Leu Thr Ala Leu Pro Asp Gly Thr Tyr Gly 1045        1055        1065        1075
CTGCTGTACGAGCCGGGCACCGGCATCAGATACGCCAACTTCAAC
Leu Leu Tyr Glu Pro Gly Thr Gly Ile Arg Tyr Ala Asn Phe Asn 1090        1100        1110        1120
CTCGCCTGGCTGGGCGGCATCTGCGCGCCCTTCACGATTCCGGAT
Leu Ala Trp Leu Gly Gly Ile Cys Ala Pro Phe Thr Ile Pro Asp 1135        1145        1155        1165
GTGGCGCTCGAGCCGGGCCAGCAGGTCACTGTTCCGGTGGCCGTC
Val Ala Leu Glu Pro Gly Gln Gln Val Thr Val Pro Val Ala Val 1180        1190        1200        1210
ACGAACCAGTCCGGTATCGCGGTACCGAAGCCGAGCCTTCAGCTC
Thr Asn Gln Ser Gly Ile Ala Val Pro Lys Pro Ser Leu Gln Leu 1225        1235        1245        1255
GACGCATCGCCGGACTGGCAGGTTCAGGGTTCCGTCGAGCCCCTC
Asp Ala Ser Pro Asp Trp Gln Val Gln Gly Ser Val Glu Pro Leu
```

-continued

```
        1270        1280        1290        1300
ATGCCCGGACGGCAGGCCAAGGGCCAGGTGACCATCACGGTTCCC
Met Pro Gly Arg Gln Ala Lys Gly Gln Val Thr Ile  Thr Val Pro 1315        1325        1335        1345
GCCGGCACCACCCCCGGTCGCTACCGGGTCGGTGCGACGCTGCGC
Ala Gly Thr Thr Pro Gly Arg Tyr Arg Val Gly Ala Thr Leu Arg 1360        1370        1380        1390
ACCTCCGCGGGTAACGCGTCGACGACCTTCACGGTCACGGTTGGA
Thr Ser Ala Gly Asn Ala Ser Thr Thr Phe Thr Val Thr Val Gly 1405        1415        1425        1435
CTGCTCGACCAGGCCCGGATGAGCATCGCGGACGTCGACAGCGAG
Leu Leu Asp Gln Ala Arg Met Ser Ile  Ala Asp Val Asp Ser Glu 1450        1460        1470        1480
GAGACCGCCCGCGAAGACGGGCGGGCGAGCAACGTGATCGACGGC
Glu Thr Ala Arg Glu Asp Gly Arg Ala Ser Asn Val Ile Asp Gly 1495        1505        1515        1525
AACCCCTCGACGTTCTGGCACACCGAATGGTCGCGTGCCGATGCT
Asn Pro Ser Thr Phe Trp His Thr Glu Trp Ser Arg Ala Asp Ala 1540        1550        1560        1570
CCTGGCTACCCGCACCGCATCAGCCTCGACCTCGGTGGCACGCAC
Pro Gly Tyr Pro His Arg Ile  Ser Leu Asp Leu Gly Gly Thr His 1585        1595        1605        1615
ACGATCAGCGGCCTCCAGTACACCCGACGGCAGAACAGCGCCAAC
Thr Ile  Ser Gly Leu Gln Tyr Thr Arg Arg Gln Asn Ser Ala Asn 1630        1640        1650        1660
GAGCAGGTCGCGGACTACGAGATCTTCGCGGTGGACCTCAGCGCC
Glu Gln Val Ala Asp Tyr Glu Ile  Phe Ala Val Asp Leu Ser Ala 1675        1685        1695        1705
GCCACCGGGCGATGTGCGTCCTGCGGTGCGGCTGGCCCCATGGCC
Ala Thr Gly Arg Cys Ala Ser Cys Gly Ala Ala Gly Pro Met Ala 1720        1730        1740        1750
GGGCTGCACGTCTTCTCCCACGCCCCCGGCCTGGTCGGCCGCTGT
Gly Leu His Val Phe Ser His Ala Pro Gly Leu Val Gly Arg Cys 1765        1775        1785        1795
CCCGCCTGTGAACAGGTGATGCTGCGGCTGGTCCGCGCCCCCGAC
Pro Ala Cys Glu Gln Val Met Leu Arg Leu Val Arg Ala Pro Asp 1810        1820        1830        1840
CGCGCCTGGCTGGACCTGCGCGGGGCCACCTACCTGCAGGTGCCG
Arg Ala Trp Leu Asp Leu Arg Gly Ala Thr Tyr Leu Gln Val Pro 1855        1865        1875
TTGGCGTTCGACCAGCCGCACCCCGGCCCGCTGTGA
Leu Ala Phe Asp Gln Pro His Pro Gly Pro Leu * * *
```

By the use of microorganisms maintaining the recombinant DNA containing DNA fragment carrying thereon genetic information that participates in synthesis of neuraminidase, neuraminidase can be produced efficiently without supplementation of any neuraminidase inducer.

What is claimed is:

1. A process for producing neuraminidase which comprises culturing in a medium a microorganism belonging to the genus Streptomyces and transformed with a recombinant DNA containing an isolated DNA fragment that consists essentially of a *M. viridifaciens* DNA fragment comprising a DNA sequence encoding a neuraminidase and no more than 500 base pairs of native 3'-flanking sequence regions, and no more than 5.2K base pairs of native 5'-flanking sequence regions, accumulating neuraminidase in a culture and recovering neuraminidase from the culture.

2. The process according to claim 1, wherein the microorganism belonging to the genus Streptomyces is *Streptomyces lividans* NED-BG6 (FERM BP-1768) or *Streptomyces lividans* NED-BC4 (FERM BP-2340).

3. A microorganism belonging to the genus Streptomyces and transformed with a recombinant DNA containing an isolated DNA fragment that consists essentially of a *M. viridifaciens* DNA fragment comprising a DNA sequence encoding a neuraminidase and no more than 500 base pairs of native 3'-flanking sequence regions, and no more than 5.2K base pairs of native 5'-flanking sequence regions.

4. The microorganism according to claim 3, which is *Streptomyces lividans* NED-BG6 (FERM BP-1768) or *Streptomyces lividans* NED-BC4 (FERM BP-2340).

5. A recombinant DNA containing an isolated DNA fragment that consists essentially of a DNA fragment comprising a *M. viridifaciens* DNA sequence encoding a neuraminidase and no more than 500 base pairs of native 3'-flanking sequence regions, and no more than 5.2K base pairs of native 5'-flanking sequence regions.

6. Recombinant DNA pNED-BG6 containing a DNA fragment which comprises a DNA sequence encoding a neuraminidase as well as flanking sequence regions, characterized in that it is 8.3 kb, and has the following numbers of restriction endonuclease cleavage sites, 2 for Bam HI, 3 for Xho I, 5 for Bcl I, 3 for Cla I, 1 for Sac I, 2 for Bgl II, 2 for Kpn and 1 for Pst I.

7. Recombinant DNA pNED-BC6 containing a DNA fragment which comprises a DNA sequence encoding a neuraminidase as well as flanking sequence regions, characterized in that it is 13.7 kb, and has the following numbers of restriction endonuclease cleavage sites, 3 for Bam HI, 3 for Xho I, 5 for Bcl I, 3 for Cla I, 1 for Sac I, 2 for Bgl II, 2 for Kpn and 3 for Pst I.

8. A gene encoding neuraminidase derived from a microorganism belonging to the genus Micromonospora represented by the DNA nucleotide sequence coding for the following amino acid sequence.

```
             10           20           30           40
ATCGCCGGGGCACCCGTCCCGCCCGGCGGCGAGCCGCTCTACACG
Ile Ala Gly Ala Pro Val Pro Pro Gly Gly Glu Pro Leu Tyr Thr 55           65           75           85
GAGCAGGACCTCGCCGTGAACGGCAGGGAGGGCTTTCCGAACTAC
Glu Gln Asp Leu Ala Val Asn Gly Arg Glu Gly Phe Pro Asn Tyr 100          110          120          130
CGCATCCCAGCGCTGACCGTCACGCCCGACGGGGACCTGCTGGCC
Arg Ile Pro Ala Leu Thr Val Thr Pro Asp Gly Asp Leu Leu Ala 145          155          165          175
TCGTACGACGGCCGCCCGACCGGTATCGACGCGCCCGGCCCCAAC
Ser Tyr Asp Gly Arg Pro Thr Gly Ile Asp Ala Pro Gly Pro Asn 190          200          210          220
TCCATCCTCCAACGCCGCAGCACCGACGGCGGCCGGACGTGGGGC
Ser Ile Leu Gln Arg Arg Ser Thr Asp Gly Gly Arg Thr Trp Gly 235          245          255          265
GAGCAACAGGTCGTCAGCGCCGGCCAGACCACCGCGCCGATCAAG
Glu Gln Gln Val Val Ser Ala Gly Gln Thr Thr Ala Pro Ile Lys 280          290          300          310
GGGTTCTCCGACCCCAGCTACCTTGTCGACCGGGAAACCGGGACC
Gly Phe Ser Asp Pro Ser Tyr Leu Val Asp Arg Glu Thr Gly Thr 325          335          345          355
ATCTTCAACTTCCACGTCTACTCCCAGCGGCAGGGCTTCGCCGGC
Ile Phe Asn Phe His Val Tyr Ser Gln Arg Gln Gly Phe Ala Gly 370          380          390          400
AGCCGGCCCGGCACCGACCCGGCAGACCCCAACGTGCTCCACGCC
Ser Arg Pro Gly Thr Asp Pro Ala Asp Pro Asn Val Leu His Ala 415          425          435          445
AACGTCGCGACCTCGACCGACGGCGGTCTGACCTGGTCGCACCGG
Asn Val Ala Thr Ser Thr Asp Gly Gly Leu Thr Trp Ser His Arg 460          470          480          490
ACCATCACGGCCGACATCACCCCCGGATCCGGGCTGGCGCAGCCGC
Thr Ile Thr Ala Asp Ile Thr Pro Asp Pro Gly Trp Arg Ser Arg 505          515          525          535
TTCGCCGCCTCCGGCGAAGGCATCCAGCTCCGCTATGGACCCCAC
Phe Ala Ala Ser Gly Glu Gly Ile Gln Leu Arg Tyr Gly Pro His 550          560          570          580
GCCGGTCGACTCATCCAGCAGTACACGATCATCAACGCTGCCGGC
Ala Gly Arg Leu Ile Gln Gln Tyr Thr Ile Ile Asn Ala Ala Gly 595          605          615          625
GCCTTCCAGGCGGTGAGCGTGTACAGCGACGACCACGGAAGGACC
Ala Phe Gln Ala Val Ser Val Tyr Ser Asp Asp His Gly Arg Thr 640          650          660          670
TGGCGCGCCGGCGAAGCCGTCGGGGTCGGCATGGACGAGAACAAG
Trp Arg Ala Gly Glu Ala Val Gly Val Gly Met Asp Glu Asn Lys 685          695          705          715
ACCGTGGAACTCTCCGATGGCCGGGTCCTGCTCAACAGCCGCGAC
Thr Val Glu Leu Ser Asp Gly Arg Val Leu Leu Asn Ser Arg Asp 730          740          750          760
TCGGCCCGCAGCGGATACCGTAAGGTGGCCGTCTCCACTGACGGC
Ser Ala Arg Ser Gly Tyr Arg Lys Val Ala Val Ser Thr Asp Gly 775          785          795          805
GGCCACAGCTACGGCCCGGTGACCATCGACCGCGACCTCCCCGAC
Gly His Ser Tyr Gly Pro Val Thr Ile Asp Arg Asp Leu Pro Asp
```

```
                820           830           840           850
CCGACGAACAACGCATCGATCATCCGGGCCTTCCCTGACGCCCCG
Pro Thr Asn Asn Ala Ser Ile Ile Arg Ala Phe Pro Asp Ala Pro 865           875           885           895
GCCGGCTCCGCGCGGGCCAAGGTCCTGCTCTTCTCCAACGCCGCC
Ala Gly Ser Ala Arg Ala Lys Val Leu Leu Phe Ser Asn Ala Ala 910           920           930           940
AGCCAGACCTCGCGCAGTCAGGGCACCATCCGGATGTCCTGCGAC
Ser Gln Thr Ser Arg Ser Gln Gly Thr Ile Arg Met Ser Cys Asp 955           965           975           985
GATGGCCAGACCTGGCCGGTTTCGAAGGTCTTCCAGCCCGGCTCG
Asp Gly Gln Thr Trp Pro Val Sel Lys Val Phe Gln Pro Gly Ser 1000          1010          1020          1030
ATGTCGTACTCCACCCTGACCGCACTGCCCGACGGCACCTACGGG
Met Ser Tyr Ser Thr Leu Thr Ala Leu Pro Asp Gly Thr Tyr Gly 1045          1055          1065          1075
CTGCTGTACGAGCCGGGCACCGGCATCAGATACGCCAACTTCAAC
Leu Leu Tyr Glu Pro Gly Thr Gly Ile Arg Tyr Ala Asn Phe Asn 1090          1100          1110          1120
CTCGCCTGGCTGGGCGGCATCTGCGCGCCCTTCACGATTCCGGAT
Leu Ala Trp Leu Gly Gly Ile Cys Ala Pro Phe Thr Ile Pro Asp 1135          1145          1155          1165
GTGGCGCTCGAGCCGGGCCAGCAGGTCACTGTTCCGGTGGCCGTC
Val Ala Leu Glu Pro Gly Gln Gln Val Thr Val Pro Val Ala Val 1180          1190          1200          1210
ACGAACCAGTCCGGTATCGCGGTACCGAAGCCGAGCCTTCAGCTC
Thr Asn Gln Ser Gly Ile Ala Val Pro Lys Pro Ser Leu Gln Leu 1225          1235          1245          1255
GACGCATCGCCGGACTGGCAGGTTCAGGGTTCCGTCGAGCCCCTC
Asp Ala Ser Pro Asp Trp Gln Val Gln Gly Ser Val Glu Pro Leu 1270          1280          1290          1300
ATGCCCGGACGGCAGGCCAAGGGCCAGGTGACCATCACGGTTCCC
Met Pro Gly Arg Gln Ala Lys Gly Gln Val Thr Ile Thr Val Pro 1315          1325          1335          1345
GCCGGCACCACCCCCGGTCGCTACCGGGTCGGTGCGACGCTGCGC
Ala Gly Thr Thr Pro Gly Arg Tyr Arg Val Gly Ala Thr Leu Arg 1360          1370          1380          1390
ACCTCCGCGGGTAACGCGTCGACGACCTTCACGGTCACGGTTGGA
Thr Ser Ala Gly Asn Ala Ser Thr Thr Phe Thr Val Thr Val Gly 1405          1415          1425          1435
CTGCTCGACCAGGCCCGGATGAGCATCGCGGACGTCGACAGCGAG
Leu Leu Asp Gln Ala Arg Met Ser Ile Ala Asp Val Asp Ser Glu 1450          1460          1470          1480
GAGACCGCCCGCGAAGACGGGCGGGCGAGCAACGTGATCGACGGC
Glu Thr Ala Arg Glu Asp Gly Arg Ala Ser Asn Val Ile Asp Gly 1495          1505          1515          1525
AACCCCTCGACGTTCTGGCACACCGAATGGTCGCGTGCCGATGCT
Asn Pro Ser Thr Phe Trp His Thr Glu Trp Ser Arg Ala Asp Ala 1540          1550          1560          1570
CCTGGCTACCCGCACCGCATCAGCCTCGACCTCGGTGGCACGCAC
Pro Gly Tyr Pro His Arg Ile Ser Leu Asp Leu Gly Gly Thr His 1585          1595          1605          1615
ACGATCAGCGGCCTCCAGTACACCCGACGGCAGAACAGCGCCAAC
Thr Ile Ser Gly Leu Gln Tyr Thr Arg Arg Gln Asn Ser Ala Asn 1630          1640          1650          1660
GAGCAGGTCGCGGACTACGAGATCTTCGCGGTGGACCTCAGCGCC
Glu Gln Val Ala Asp Tyr Glu Ile Phe Ala Val Asp Leu Ser Ala 1675          1685          1695          1705
GCCACCGGGCGATGTGCGTCCTGCGGTGCGGCTGGCCCCATGGCC
Ala Thr Gly Arg Cys Ala Ser Cys Gly Ala Ala Gly Pro Met Ala
```

```
                 1720      1730      1740       1750
             GGGCTGCACGTCTTCTCCCACGCCCCCGGCCTGGTCGGCCGCTGT
             Gly Leu His Val Phe Ser His Ala Pro Gly Leu Val Gly Arg Cys 1765      1775      1785       1795
             CCCGCCTGTGAACAGGTGATGCTGCGGCTGGTCCGCGCCCCCGAC
             Pro Ala Cys Glu Gln Val Met Leu Arg Leu Val Arg Ala Pro Asp 1810      1820      1830       1840
             CGCGCCTGGCTGGACCTGCGCGGGGCCACCTACCTGCAGGTGCCG
             Arg Ala Trp Leu Asp Leu Arg Gly Ala Thr Tyr Leu Gln Val Pro 1855      1865       1875
             TTGGCGTTCGACCAGCCGCACCCCGGCCCGCTGTGA
             Leu Ala Phe Asp Gln Pro His Pro Gly Pro Leu * * *.
```

9. The process according to claim 1, wherein the isolated DNA fragment contains the nucleotide sequence coding for the following amino acid sequence.

```
             10        20        30         40
     ATCGCCGGGGCACCCGTCCCGCCCGGCGGCGAGCCGCTCTACACG
     Ile Ala Gly Ala Pro Val Pro Pro Gly Gly Glu Pro Leu Tyr Thr 55        65        75         85
     GAGCAGGACCTCGCCGTGAACGGCAGGGAGGGCTTTCCGAACTAC
     Glu Gln Asp Leu Ala Val Asn Gly Arg Glu Gly Phe Pro Asn Tyr 100       110       120        130
     CGCATCCCAGCGCTGACCGTCACGCCCGACGGGGACCTGCTGGCC
     Arg Ile Pro Ala Leu Thr Val Thr Pro Asp Gly Asp Leu Leu Ala 145       155       165        175
     TCGTACGACGGCCGCCCGACCGGTATCGACGCGCCCGGCCCCAAC
     Ser Tyr Asp Gly Arg Pro Thr Gly Ile Asp Ala Pro Gly Pro Asn 190       200       210        220
     TCCATCCTCCAACGCCGCAGCACCGACGGCGGCCGGACGTGGGGC
     Ser Ile Leu Gln Arg Arg Ser Thr Asp Gly Gly Arg Thr Trp Gly 235       245       255        265
     GAGCAACAGGTCGTCAGCGCCGGCCAGACCACCGCGCCGATCAAG
     Glu Gln Gln Val Val Ser Ala Gly Gln Thr Thr Ala Pro Ile Lys 280       290       300        310
     GGGTTCTCCGACCCCAGCTACCTTGTCGACCGGGAAACCGGGACC
     Gly Phe Ser Asp Pro Ser Tyr Leu Val Asp Arg Glu Thr Gly Thr 325       335       345        355
     ATCTTCAACTTCCACGTCTACTCCCAGCGGCAGGGCTTCGCCGGC
     Ile Phe Asn Phe His Val Tyr Ser Gln Arg Gln Gly Phe Ala Gly 370       380       390        400
     AGCCGGCCCGGCACCGACCCGGCAGACCCCAACGTGCTCCACGCC
     Ser Arg Pro Gly Thr Asp Pro Ala Asp Pro Asn Val Leu His Ala 415       425       435        445
     AACGTCGCGACCTCGACCGACGGCGGTCTGACCTGGTCGCACCGG
     Asn Val Ala Thr Ser Thr Asp Gly Gly Leu Thr Trp Ser His Arg 460       470       480        490
     ACCATCACGGCCGACATCACCCCGGATCCGGGCTGGCGCAGCCGC
     Thr Ile Thr Ala Asp Ile Thr Pro Asp Pro Gly Trp Arg Ser Arg 505       515       525        535
     TTCGCCGCCTCCGGCGAAGGCATCCAGCTCCGCTATGGACCCCAC
     Phe Ala Ala Ser Gly Glu Gly Ile Gln Leu Arg Tyr Gly Pro His 550       560       570        580
     GCCGGTCGACTCATCCAGCAGTACACGATCATCAACGCTGCCGGC
     Ala Gly Arg Leu Ile Gln Gln Tyr Thr Ile Ile Asn Ala Ala Gly 595       605       615        625
     GCCTTCCAGGCGGTGAGCGTGTACAGCGACGACCACGGAAGGACC
     Ala Phe Gln Ala Val Ser Val Tyr Ser Asp Asp His Gly Arg Thr 640       650       660        670
     TGGCGCGCCGGCGAAGCCGTCGGGGTCGGCATGGACGAGAACAAG
     Trp Arg Ala Gly Glu Ala Val Gly Val Gly Met Asp Glu Asn Lys
```

```
              685           695           705           715
ACCGTGGAACTCTCCGATGGCCGGGTCCTGCTCAACAGCCGCGAC
Thr Val Glu Leu Ser Asp Gly Arg Val Leu Leu Asn Ser Arg Asp 730           740           750           760
TCGGCCCGCAGCGGATACCGTAAGGTGGCCGTCTCCACTGACGGC
Ser Ala Arg Ser Gly Tyr Arg Lys Val Ala Val Ser Thr Asp Gly 775           785           795           805
GGCCACAGCTACGGCCCGGTGACCATCGACCGCGACCTCCCCGAC
Gly His Ser Tyr Gly Pro Val Thr Ile Asp Arg Asp Leu Pro Asp 820           830           840           850
CCGACGAACAACGCATCGATCATCCGGGCCTTCCCTGACGCCCCG
Pro Thr Asn Asn Ala Ser Ile Ile Arg Ala Phe Pro Asp Ala Pro 865           875           885           895
GCCGGCTCCGCGCGGGCCAAGGTCCTGCTCTTCTCCAACGCCGCC
Ala Gly Ser Ala Arg Ala Lys Val Leu Leu Phe Ser Asn Ala Ala 910           920           930           940
AGCCAGACCTCGCGCAGTCAGGGCACCATCCGGATGTCCTGCGAC
Ser Gln Thr Ser Arg Ser Gln Gly Thr Ile Arg Met Ser Cys Asp 955           965           975           985
GATGGCCAGACCTGGCCGGTTTCGAAGGTCTTCCAGCCCGGCTCG
Asp Gly Gln Thr Trp Pro Val Sel Lys Val Phe Gln Pro Gly Ser 1000          1010          1020          1030
ATGTCGTACTCCACCCTGACCGCACTGCCCGACGGCACCTACGGG
Met Ser Tyr Ser Thr Leu Thr Ala Leu Pro Asp Gly Thr Tyr Gly 1045          1055          1065          1075
CTGCTGTACGAGCCGGGCACCGGCATCAGATACGCCAACTTCAAC
Leu Leu Tyr Glu Pro Gly Thr Gly Ile Arg Tyr Ala Asn Phe Asn 1090          1100          1110          1120
CTCGCCTGGCTGGGCGGCATCTGCGCGCCCTTCACGATTCCGGAT
Leu Ala Trp Leu Gly Gly Ile Cys Ala Pro Phe Thr Ile Pro Asp 1135          1145          1155          1165
GTGGCGCTCGAGCCGGGCCAGCAGGTCACTGTTCCGGTGGCCGTC
Val Ala Leu Glu Pro Gly Gln Gln Val Thr Val Pro Val Ala Val 1180          1190          1200          1210
ACGAACCAGTCCGGTATCGCGGTACCGAAGCCGAGCCTTCAGCTC
Thr Asn Gln Ser Gly Ile Ala Val Pro Lys Pro Ser Leu Gln Leu 1225          1235          1245          1255
GACGCATCGCCGGACTGGCAGGTTCAGGGTTCCGTCGAGCCCCTC
Asp Ala Ser Pro Asp Trp Gln Val Gln Gly Ser Val Glu Pro Leu 1270          1280          1290          1300
ATGCCCGGACGGCAGGCCAAGGGCCAGGTGACCATCACGGTTCCC
Met Pro Gly Arg Gln Ala Lys Gly Gln Val Thr Ile Thr Val Pro 1315          1325          1335          1345
GCCGGCACCACCCCCGGTCGCTACCGGGTCGGTGCGACGCTGCGC
Ala Gly Thr Thr Pro Gly Arg Tyr Arg Val Gly Ala Thr Leu Arg 1360          1370          1380          1390
ACCTCCGCGGGTAACGCGTCGACGACCTTCACGGTCACGGTTGGA
Thr Ser Ala Gly Asn Ala Ser Thr Thr Phe Thr Val Thr Val Gly 1405          1415          1425          1435
CTGCTCGACCAGGCCCGGATGAGCATCGCGGACGTCGACAGCGAG
Leu Leu Asp Gln Ala Arg Met Ser Ile Ala Asp Val Asp Ser Glu 1450          1460          1470          1480
GAGACCGCCCGCGAAGACGGGCGGGCGAGCAACGTGATCGACGGC
Glu Thr Ala Arg Glu Asp Gly Arg Ala Ser Asn Val Ile Asp Gly 1495          1505          1515          1525
AACCCCTCGACGTTCTGGCACACCGAATGGTCGCGTGCCGATGCT
Asn Pro Ser Thr Phe Trp His Thr Glu Trp Ser Arg Ala Asp Ala 1540          1550          1560          1570
CCTGGCTACCCGCACCGCATCAGCCTCGACCTCGGTGGCACGCAC
Pro Gly Tyr Pro His Arg Ile Ser Leu Asp Leu Gly Gly Thr His
```

```
              1585          1595          1605          1615
ACGATCAGCGGCCTCCAGTACACCCGACGGCAGAACAGCGCCAAC
Thr Ile Ser Gly Leu Gln Tyr Thr Arg Arg Gln Asn Ser Ala Asn 1630          1640          1650          1660
GAGCAGGTCGCGGACTACGAGATCTTCGCGGTGGACCTCAGCGCC
Glu Gln Val Ala Asp Tyr Glu Ile Phe Ala Val Asp Leu Ser Ala 1675          1685          1695          1705
GCCACCGGGCGATGTGCGTCCTGCGGTGCGGCTGGCCCCATGGCC
Ala Thr Gly Arg Cys Ala Ser Cys Gly Ala Ala Gly Pro Met Ala 1720          1730          1740          1750
GGGCTGCACGTCTTCTCCCACGCCCCCGGCCTGGTCGGCCGCTGT
Gly Leu His Val Phe Ser His Ala Pro Gly Leu Val Gly Arg Cys 1765          1775          1785          1795
CCCGCCTGTGAACAGGTGATGCTGCGGCTGGTCCGCGCCCCCGAC
Pro Ala Cys Glu Gln Val Met Leu Arg Leu Val Arg Ala Pro Asp 1810          1820          1830          1840
CGCGCCTGGCTGGACCTGCGCGGGGCCACCTACCTGCAGGTGCCG
Arg Ala Trp Leu Asp Leu Arg Gly Ala Thr Tyr Leu Gln Val Pro 1855          1865          1875
TTGGCGTTCGACCAGCCGCACCCCGGCCCGCTGTGA
Leu Ala Phe Asp Gln Pro His Pro Gly Pro Leu ***.
```

10. The recombinant isolated DNA according to claim 5, wherein the DNA fragment contains the nucleotide sequence coding for the following amino acid sequence.

```
        10           20           30           40
ATCGCCGGGGCACCCGTCCCGCCCGGCGGCGAGCCGCTCTACACG
Ile Ala Gly Ala Pro Val Pro Pro Gly Gly Glu Pro Leu Tyr Thr 55           65           75           85
GAGCAGGACCTCGCCGTGAACGGCAGGGAGGGCTTTCCGAACTAC
Glu Gln Asp Leu Ala Val Asn Gly Arg Glu Gly Phe Pro Asn Tyr 100          110          120          130
CGCATCCCAGCGCTGACCGTCACGCCCGACGGGGACCTGCTGGCC
Arg Ile Pro Ala Leu Thr Val Thr Pro Asp Gly Asp Leu Leu Ala 145          155          165          175
TCGTACGACGGCCGCCCGACCGGTATCGACGCGCCCGGCCCCAAC
Ser Tyr Asp Gly Arg Pro Thr Gly Ile Asp Ala Pro Gly Pro Asn 190          200          210          220
TCCATCCTCCAACGCCGCAGCACCGACGGCGGCCGGACGTGGGGC
Ser Ile Leu Gln Arg Arg Ser Thr Asp Gly Gly Arg Thr Trp Gly 235          245          255          265
GAGCAACAGGTCGTCAGCGCCGGCCAGACCACCGCGCCGATCAAG
Glu Gln Gln Val Val Ser Ala Gly Gln Thr Thr Ala Pro Ile Lys 280          290          300          310
GGGTTCTCCGACCCCAGCTACCTTGTCGACCGGGAAACCGGGACC
Gly Phe Ser Asp Pro Ser Tyr Leu Val Asp Arg Glu Thr Gly Thr 325          335          345          355
ATCTTCAACTTCCACGTCTACTCCCAGCGGCAGGGCTTCGCCGGC
Ile Phe Asn Phe His Val Tyr Ser Gln Arg Gln Gly Phe Ala Gly 370          380          390          400
AGCCGGCCCGGCACCGACCCGGCAGACCCCAACGTGCTCCACGCC
Ser Arg Pro Gly Thr Asp Pro Ala Asp Pro Asn Val Leu His Ala 415          425          435          445
AACGTCGCGACCTCGACCGACGGCGGTCTGACCTGGTCGCACCGG
Asn Val Ala Thr Ser Thr Asp Gly Gly Leu Thr Trp Ser His Arg 460          470          480          490
ACCATCACGGCCGACATCACCCCGGATCCGGGCTGGCGCAGCCGC
Thr Ile Thr Ala Asp Ile Thr Pro Asp Pro Gly Trp Arg Ser Arg
```

```
             505              515              525              535
TTCGCCGCCTCCGGCGAAGGCATCCAGCTCCGCTATGGACCCCAC
Phe Ala Ala Ser Gly Glu Gly Ile Gln Leu Arg Tyr Gly Pro His 550              560              570              580
GCCGGTCGACTCATCCAGCAGTACACGATCATCAACGCTGCCGGC
Ala Gly Arg Leu Ile Gln Gln Tyr Thr Ile Ile Asn Ala Ala Gly 595              605              615              625
GCCTTCCAGGCGGTGAGCGTGTACAGCGACGACCACGGAAGGACC
Ala Phe Gln Ala Val Ser Val Tyr Ser Asp Asp His Gly Arg Thr 640              650              660              670
TGGCGCGCCGGCGAAGCCGTCGGGGTCGGCATGGACGAGAACAAG
Trp Arg Ala Gly Glu Ala Val Gly Val Gly Met Asp Glu Asn Lys 685              695              705              715
ACCGTGGAACTCTCCGATGGCCGGGTCCTGCTCAACAGCCGCGAC
Thr Val Glu Leu Ser Asp Gly Arg Val Leu Leu Asn Ser Arg Asp 730              740              750              760
TCGGCCCGCAGCGGATACCGTAAGGTGGCCGTCTCCACTGACGGC
Ser Ala Arg Ser Gly Tyr Arg Lys Val Ala Val Ser Thr Asp Gly 775              785              795              805
GGCCACAGCTACGGCCCGGTGACCATCGACCGCGACCTCCCCGAC
Gly His Ser Tyr Gly Pro Val Thr Ile Asp Arg Asp Leu Pro Asp 820              830              840              850
CCGACGAACAACGCATCGATCATCCGGGCCTTCCCTGACGCCCCG
Pro Thr Asn Asn Ala Ser Ile Ile Arg Ala Phe Pro Asp Ala Pro 865              875              885              895
GCCGGCTCCGCGCGGGCCAAGGTCCTGCTCTTCTCCAACGCCGCC
Ala Gly Ser Ala Arg Ala Lys Val Leu Leu Phe Ser Asn Ala Ala 910              920              930              940
AGCCAGACCTCGCGCAGTCAGGGCACCATCCGGATGTCCTGCGAC
Ser Gln Thr Ser Arg Ser Gln Gly Thr Ile Arg Met Ser Cys Asp 955              965              975              985
GATGGCCAGACCTGGCCGGTTTCGAAGGTCTTCCAGCCCGGCTCG
Asp Gly Gln Thr Trp Pro Val Sel Lys Val Phe Gln Pro Gly Ser 1000             1010             1020             1030
ATGTCGTACTCCACCCTGACCGCACTGCCCGACGGCACCTACGGG
Met Ser Tyr Ser Thr Leu Thr Ala Leu Pro Asp Gly Thr Tyr Gly 1045             1055             1065             1075
CTGCTGTACGAGCCGGGCACCGGCATCAGATACGCCAACTTCAAC
Leu Leu Tyr Glu Pro Gly Thr Gly Ile Arg Tyr Ala Asn Phe Asn 1090             1100             1110             1120
CTCGCCTGGCTGGGCGGCATCTGCGCGCCCTTCACGATTCCGGAT
Leu Ala Trp Leu Gly Gly Ile Cys Ala Pro Phe Thr Ile Pro Asp 1135             1145             1155             1165
GTGGCGCTCGAGCCGGGCCAGCAGGTCACTGTTCCGGTGGCCGTC
Val Ala Leu Glu Pro Gly Gln Gln Val Thr Val Pro Val Ala Val 1180             1190             1200             1210
ACGAACCAGTCCGGTATCGCGGTACCGAAGCCGAGCCTTCAGCTC
Thr Asn Gln Ser Gly Ile Ala Val Pro Lys Pro Ser Leu Gln Leu 1225             1235             1245             1255
GACGCATCGCCGGACTGGCAGGTTCAGGGTTCCGTCGAGCCCCTC
Asp Ala Ser Pro Asp Trp Gln Val Gln Gly Ser Val Glu Pro Leu 1270             1280             1290             1300
ATGCCCGGACGGCAGGCCAAGGGCCAGGTGACCATCACGGTTCCC
Met Pro Gly Arg Gln Ala Lys Gly Gln Val Thr Ile Thr Val Pro 1315             1325             1335             1345
GCCGGCACCACCCCCGGTCGCTACCGGGTCGGTGCGACGCTGCGC
Ala Gly Thr Thr Pro Gly Arg Tyr Arg Val Gly Ala Thr Leu Arg 1360             1370             1380             1390
ACCTCCGCGGGTAACGCGTCGACGACCTTCACGGTCACGGTTGGA
Thr Ser Ala Gly Asn Ala Ser Thr Thr Phe Thr Val Thr Val Gly
```

-continued

```
        1405          1415          1425          1435
CTGCTCGACCAGGCCCGGATGAGCATCGCGGACGTCGACAGCGAG
Leu Leu Asp Gln Ala Arg Met Ser Ile Ala Asp Val Asp Ser Glu 1450          1460          1470          1480
GAGACCGCCCGCGAAGACGGGCGGGCGAGCAACGTGATCGACGGC
Glu Thr Ala Arg Glu Asp Gly Arg Ala Ser Asn Val Ile Asp Gly 1495          1505          1515          1525
AACCCCTCGACGTTCTGGCACACCGAATGGTCGCGTGCCGATGCT
Asn Pro Ser Thr Phe Trp His Thr Glu Trp Ser Arg Ala Asp Ala 1540          1550          1560          1570
CCTGGCTACCCGCACCGCATCAGCCTCGACCTCGGTGGCACGCAC
Pro Gly Tyr Pro His Arg Ile Ser Leu Asp Leu Gly Gly Thr His 1585          1595          1605          1615
ACGATCAGCGGCCTCCAGTACACCCGACGGCAGAACAGCGCCAAC
Thr Ile Ser Gly Leu Gln Tyr Thr Arg Arg Gln Asn Ser Ala Asn 1630          1640          1650          1660
GAGCAGGTCGCGGACTACGAGATCTTCGCGGTGGACCTCAGCGCC
Glu Gln Val Ala Asp Tyr Glu Ile Phe Ala Val Asp Leu Ser Ala 1675          1685          1695          1705
GCCACCGGGCGATGTGCGTCCTGCGGTGCGGCTGGCCCCATGGCC
Ala Thr Gly Arg Cys Ala Ser Cys Gly Ala Ala Gly Pro Met Ala 1720          1730          1740          1750
GGGCTGCACGTCTTCTCCCACGCCCCCGGCCTGGTCGGCCGCTGT
Gly Leu His Val Phe Ser His Ala Pro Gly Leu Val Gly Arg Cys 1765          1775          1785          1795
CCCGCCTGTGAACAGGTGATGCTGCGGCTGGTCCGCGCCCCCGAC
Pro Ala Cys Glu Gln Val Met Leu Arg Leu Val Arg Ala Pro Asp 1810          1820          1830          1840
CGCGCCTGGCTGGACCTGCGCGGGGCCACCTACCTGCAGGTGCCG
Arg Ala Trp Leu Asp Leu Arg Gly Ala Thr Tyr Leu Gln Val Pro 1855          1865          1875
TTGGCGTTCGACCAGCCGCACCCCGGCCCGCTGTGA
Leu Ala Phe Asp Gln Pro His Pro Gly Pro Leu ***.
```

* * * * *